United States Patent [19]

Allport

[11] 4,266,425
[45] May 12, 1981

[54] METHOD FOR CONTINUOUSLY DETERMINING THE COMPOSITION AND MASS FLOW OF BUTTER AND SIMILAR SUBSTANCES FROM A MANUFACTURING PROCESS

[75] Inventor: John J. Allport, Saratoga, Calif.

[73] Assignee: Zikonix Corporation, Sunnyvale, Calif.

[21] Appl. No.: 92,983

[22] Filed: Nov. 9, 1979

[51] Int. Cl.³ ............... G01N 33/06; G01N 23/203; G01N 27/22
[52] U.S. Cl. .................................. 73/61 R; 250/272
[58] Field of Search ............ 73/61 R, 53, 32 R; 250/272, 273; 364/550, 556; 324/61 R

[56] References Cited
U.S. PATENT DOCUMENTS 4,045,657  8/1977  Falke .
4,168,431  9/1979  Henriksen .
4,193,116  3/1980  Funk ................................. 364/556

Primary Examiner—Gerald Goldberg
Assistant Examiner—Joseph W. Roskos
Attorney, Agent, or Firm—Thomas Schneck

[57] ABSTRACT

A method for continuously determining the water and fat content of a material such as butter which involves instantaneous measurements of the density of the substance, as well as either the dielectric constant or radiative backscatter intensity. Signals representing these non-destructive measurements are fed to a computer and compared with values of the same parameters which were previously measured by laboratory destructive tests. The comparison permits a calculation of the composition of the substance, specifically fat and water content. In the case of a salted material, salt content can also be calculated.

12 Claims, 2 Drawing Figures

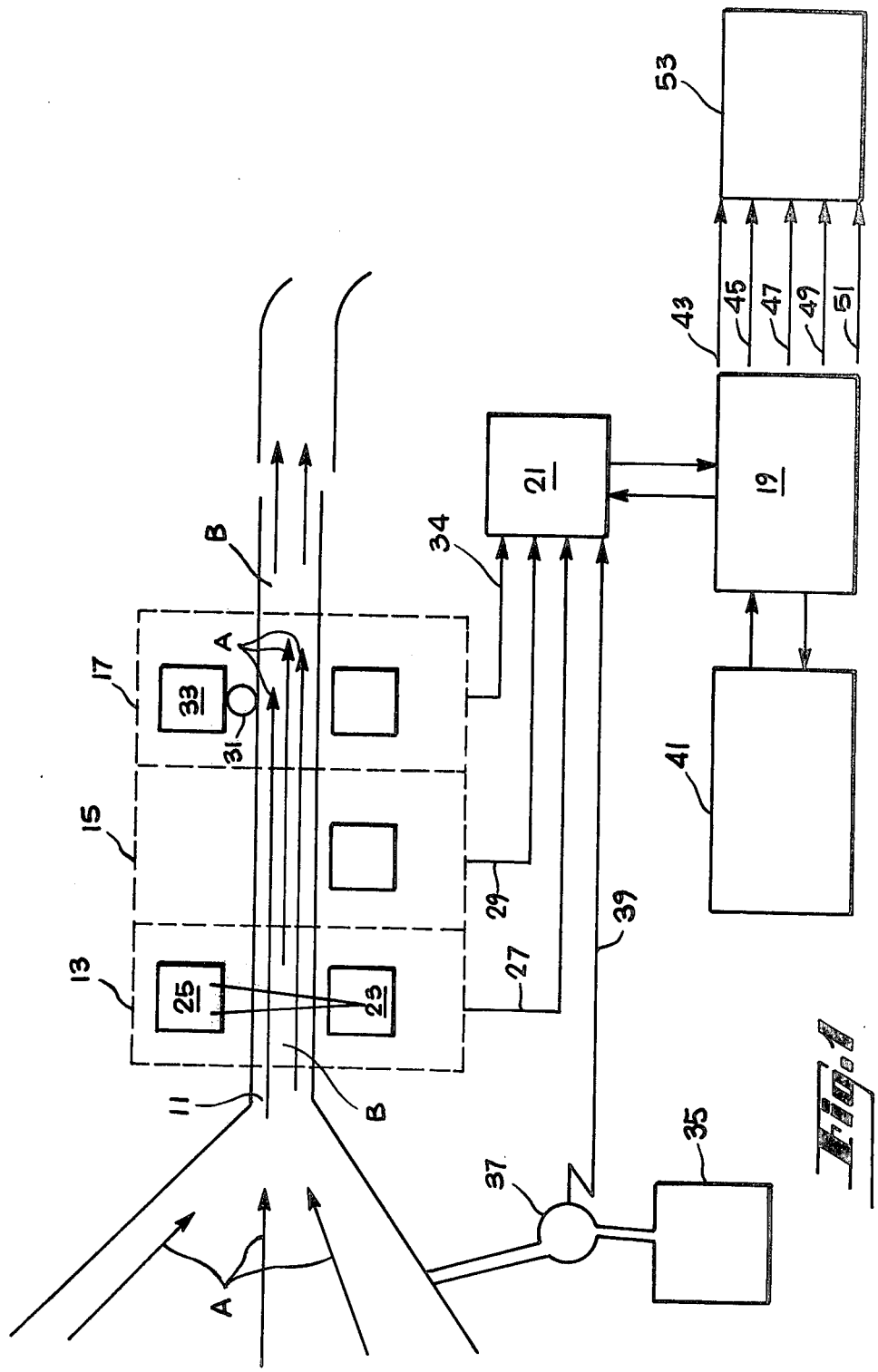

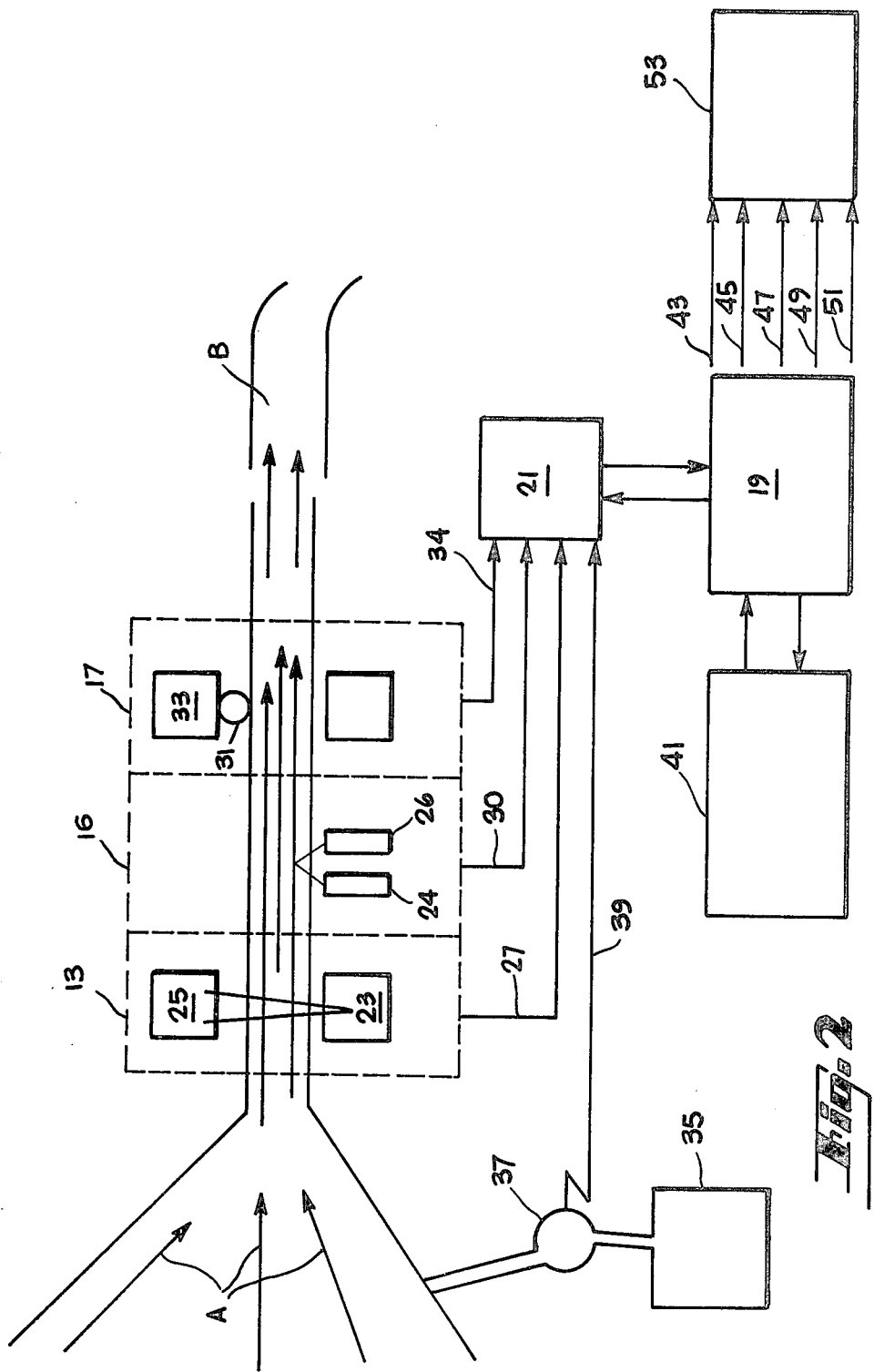

METHOD FOR CONTINUOUSLY DETERMINING THE COMPOSITION AND MASS FLOW OF BUTTER AND SIMILAR SUBSTANCES FROM A MANUFACTURING PROCESS

BACKGROUND OF THE INVENTION a. Field of the Invention

The invention relates to the measurement of the instantaneous composition and mass flow of butter and similar substances from a manufacturing process.

b. Prior Art

In the production of butter by machines, the fat and moisture content of the product must be closely regulated. Moisture gauges have been built previously to directly sense moisture in butter, but the gauges are far from accurate. The moisture usually has been sensed capacitively, using radio frequency sensors. However, the dielectric constant, which determines capacitance, varied not only with mositure, but also with density, a parameter not measured or detected by the prior mositure gauges. Density varies in butter because of different amounts of air introduced by the churning process. Although some butter machines emply vacuum sections to remove the air, the density variation still is large enough to render the dielectric constant measurement commercially useless as an indicator of mositure content.

Gamma-ray and X-ray gauges have been developed for determining material density by measuring the transmission of radiation through the material. The ratio (R) of radiation transmitted through the material ($I_1$) to that detected in the absence of the material ($I_o$) may be written:

$$R = \frac{I_1}{I_o} = e^{-\mu\rho T} \qquad (1)$$

where $\mu$ is the apparent mass absorption coefficient, $\rho$ is the unknown density and T is the thickness of the material. In a closed pipe, completely filled with the material, $I_1$ and $I_o$ can be measured with radiation detectors, and since the thickness T is known the density may be determined on a continuous basis.

The composition of simple, essentially binary, mixtures such as butter (water and fat) have been shown to be measurable in the prior art using backscattered X-ray or gamma-ray radiation.

In another invention, owned by the assignee of this invention, E. Dahlin has shown how a feedback control system using butter density and mositure content control signals, can be used as important parameters in operating a butter machine. While a static density and moisture control signals could be generated, for example by laboratory measurement, dynamic signals are preferable. By "dynamic signal" is meant a continuous real time or instantaneous measurement, as the butter is produced.

The need for a dynamic composition measurement signal exists not only in butter production, but in many industrial process applications, where the composition of the end product is slightly variable and knowledge of the variations is important.

In the same previously mentioned invention by E. Dahlin, a need is shown for measurement of the mass flow of butter from a butter machine. While average mass may be determined by weighing the product produced over a period of time, it is better to have a continuous measurement represented by a dynamic signal. A mass flow determination from a butter machine requires a real time density measurement, together with a measure of the butter flow velocity at a known dimensional cross section.

SUMMARY OF THE INVENTION

An object of the invention is to accurately measure the instantaneous composition, namely moisture and fat content, as well as the instantaneous mass flow of butter and salt content to provide signals for use in generating control signals for butter production.

The above object has been met with a non-destructive method for determining the fat and water content of butter and similar substances. In the case of salted butter and similar substances mass flow and salt content are also measured.

The method of this invention relies on continuously measuring the density of the substance as it emerges from the manufacturing process. A simultaneous continuous measurement is made of either the dielectric constant or the radiation backscatter intensity. Either one of the latter measurements provides information which can be combined with density information for a determination of substance composition.

In the case of a salted substance brine flow into the manufacturing process is also measured. A measurement of the butter mass flow is also needed in order to convert the brine flow information into a salt content determination. Mass flow is continuously determined by measuring the velocity of the substance out of the process and combining the density measurement with the velocity measurement.

All of the measured information is gathered nondestructively and fed to a computer. The computer has a memory wherein calibration data from prior test is stored. By comparing the calibration data with the measured dielectric constant or backscatter intensity, the measured density, the known curd content, the velocity, and in the case of a salted substance the brine flow, composition and mass flow of the substance may be calculated. Specifically, water, fat, mass flow, and in the case of a salted substance, the salt content are calculated for process control purposes.

BRIEF DESCRIPTION OF THE DRAWINGS

FIG. 1 is a plan view of a measurement system for continuously determining the composition and mass flow of butter from a butter machine in accord with the present invention.

FIG. 2 is a plan view of an alternate measurement system for continuously determining the composition and mass flow of butter from a butter machine in accord with the present invention.

DESCRIPTION OF THE PREFERRED EMBODIMENT

With reference to FIG. 1, the output of a butter machine is schematically depicted by arrows A. Such a machine has a silo which feeds cream into the machine where blades churn the cream causing formation of large butter globules after a time. These globules are carried into a separator section where a device such as screen or a centrifugal rotor causes separation of the butter and further agglomeration from the buttermilk. Water and brine may be added through a pipe by a control valve to provide the desired moisture content to the butter which is advanced by an auger.

An auger compresses the butter and works it into a mass which is extruded from a duct 11. This explanation of a butter machine is greatly simplified. Many machines include auxiliary features, such as a vacuum section and other blending sections. From the duct 11, a column of butter B emerges which is advanced in the direction of the arrow A by continuous motion of the auger.

In accord with the present invention, the auger provides the power for continuously advancing a column of butter B through a duct having a constant dimensional cross section containing a measuring section which is positioned near the machine outlet. The dimensions of the duct 11 determine the cross section of the butter column.

The measuring station consists of a radio isotope density sensor 13, a capacitive mositure sensor 15 and a velocimeter 17. Each of these sensors produces an electrical output signal which is electrically connected to a digital computer 19 having an auxiliary memory. This connection is achieved through a computer interface 21 which serves to convert analog signals to a digital format and to multiplex the signals. In accord with the present invention the memory of computer 19 is loaded with calibration information regarding the measured densities of butter for various known fat and moisture contents which can be made using the butter machine. Different densities can be achieved by operating the machine with different beater speeds, auger speeds, as well as by applying different doses of moisture or brine. Other differences in density arise from differences in the composition of the cream used or because of different amounts of air are entrained in the production process.

The density of the butter is measured by the density sensor 13. This sensor is of a known transmissive X-ray or radioisotope type. A radioactive source, such as Americium 241 is housed in canister 23. Such a source emits gamma rays with a principal energy peak at 59.7 kev. A detector 25 is positioned on the opposite side of butter column B so that the gamma rays passing through the aperture of detector 43 have passed through the butter column B. The detector 43 is of the type which produces an electrical signal proportional to the intensity ($I_1$) of gamma rays which are detected. This electrical signal is transmitted along line 27 to the computer interface 21. Prior to reading the gamma ray intensity through the butter, an intensity signal ($I_o$) is measured in the absence of butter. The computer 19 then computes the ratio R of the intensities in accord with equation (1). Since the transverse dimension of the sample is known from the dimensions of the duct 11 and since at 59.7 kev the apparent mass absorption coefficient for butter is known and is not essentially composition dependent, the unknown density may be calculated from equation (1). This calculation is made in computer 19. The computer is able to compute density as fast as radiation intensity signals are received and so the computer is able to produce a dynamic signal representing the instantaneous density of butter as it emerges from the butter machine.

If the density is known, moisture content may be measured either by means of radio frequency techniques which sense the dielectric constant of the butter, or alternatively the composition may be determined by measuring the intensity of backscattered X-ray or gamma-ray radiation at a properly chosen energy as will be seen below.

At the same time that density is being measured, the instantaneous dielectric constant of the butter column is also being measured by the sensor 15. This is a capacitive sensor which measures dielectric constant in the radio frequency spectrum. Such devices are known in prior art and one such dielectric constant sensor is manufactured by Brabender Messtechnik of Duisburg, W. Germany. An explanation of this type of dielectric constant sensor is contained in the article "Kontinuierliche Wassergehaltsmessung an Butter" by W. Heinz. Preferred radio frequencies are in the range from 1 MHz to 100 MHz. Microwave propagation and reflection techniques may also be employed. They introduce more complexity however, with no increase in accuracy. This gives a dynamic signal transmitted along line 29, with signal strength or intensity functionally dependent on the dielectric constant of the butter. In turn, the dielectric constant is proportional to moisture content and density in accord with known relationships. For example, Table I in the above mentioned article shows that when the percentage of water in butter varies from 0 to 30% the corresponding measured dielectric constant ranges from 3.2 to 11.6. The memory of the computer contains information indicating how the dielectric constant of the butter varies with composition and density. Once the measured dielectric constant and measured density as well as the known curd content signals are fed into the computer the composition (water and fat content) may be calculated.

The finished butter moves as a mass through the duct 11 of known cross section from the machine. The velocity may therefore be measured by acoustical or optical doppler shift measurements or by means of a wheel 31 which is turned by butter motion which in turn drives a rotary encoder 33. A velocity signal is transmitted to the computer along line 34. Once the velocity is known and the instantaneous density is known, the mass flow can be computed in the usual manner using the known duct cross section.

In the event that brine is introduced from a supply 35 into the butter machine through a valve 37 so that salted butter is produced, the flow rate of the brine is measured at a valve introducing the brine into the manufacturing process and a signal representing this flow rate is transmitted along line 39 to the computer 19 via interface 21. Since the brine has a known salt content, the flow rate, together with the mass flow rate of butter, indicates the amount of salt being introduced into the butter. This information is useful since the salt content also affects the dielectric constant measurement. The memory of the computer also contains information indicating the manner in which the dielectric constant of the butter varies with salt content. Once the salt content signal is fed to the computer together with the dielectric constant, the density, and the known curd content the composition (water and fat content) may be calculated continuously. The same is done when no brine signal is present.

Computer 19 also receives data from a laboratory 41 where the cream and butter are periodically tested for curd content. The curd content of the butter produced in a given machine has been found to correlate directly with the curd content in cream and the fat content in the butter. Before the machine is started the curd content of the cream in the silo is measured and used to determine the curd content expected in the butter. This value of curd content is entered into the computer as an initial value. Once the butter production has started a sample of the butter is taken and quickly analyzed in the laboratory for curd content, this value is then entered into the computer and used as the known curd content for the rest of the production run. Similarly, the salt content of the brine is measured and remains unchanged in the manufacturing process. Signals reprenting this data are transmitted from laboratory 41 to computer 19 on a periodic basis, as needed.

The computer is able to compute the fat, moisture and salt content by comparing the measured values of the parameters mentioned above, such as density, dielectric constant, mass flow, brine flow and curd content with data from calibration trials where each of the parameters was measured in the laboratory by test. The test data is stored in the computer for different runs of the butter machine representing the conditions under which the machine is expected to operate.

The output of the computer 19 includes butterfat content taken along line 43, the water content on line 45, the salt content, if any, on line 47, the curd content on line 49 and the mass flow on line 51. These outputs are transmitted to a control panel 53 for a butter machine where the data may be viewed, recorded and used to control process operation.

FIG. 2 illustrates an alternate means of measuring the corrected density of the butter. The system is the same as in FIG. 1 except that the dielectric constant sensor 15 is replaced by a backscatter sensor 16. A radioactive source is housed in a canister 24 similar to the source housed in canister 23. Low energies provide the best discrimination, however they also represent instrumental problems. In the case of butter a good choice is X-ray or gamma-ray radiation in the approximate energy range 15 to 25 kev. The density is best measured using X-ray or gamma-ray radiation of higher energy such that it is not affected by the composition variances which may occur. For butter, one chooses energies in excess of 45 kev. A radiation detector is housed in the canister 26, similar to the canister 25. The detector in canister 26 is positioned for measuring radiation backscattered from the butter column. The backscatter intensity is inversely proportional to the photoelectric cross section of the butter. It is well known that water molecules have a higher photoelectric cross section than fat molecules. Accordingly, intensity of backscattered radiation decreases as the percentage of water increases. A signal proportional to the backscattered intensity is taken along line 30 and transmitted to the computer. The radiation source might be an Americium 241 source with a Beryllium window which permits emission of the Neptunium L X-rays of average energe about 17.7 kev which are nearly ideal in energy for determining the composition of butter. The detector housed in canister 26 is optimized for detecting the neptunium L X-rays and is made insensitive to the 59.7 kev Americium 241 gamma rays. The measured density is used to provide minor corrections, as required, to the composition as determined from the backscattered energy at 17.7 kev.

When salted butter is produced, the backscattered intensity depends on the salt content as well as the water and fat content because the photoelectric absorption cross sections of sodium and chlorine are considerably larger than those of butterfat and water at the low energies employed. The measured brine flow rate and the measured butter mass flow rate are determined however, as described earlier, and are used to determine the salt content of the butter. The determined salt content, the known curd content, together with the density, and the backscattered intensity, along with calibration data stored in the computer are then used to determine the butter composition, namely water and fat content as previously described.

While this invention has been described with reference to butter production, the same system may be applied to the production of margarine and to liquid dairy products, as well as other essentially binary or tertiary products.

What is claimed is:

1. A non-destructive method for continuously determining the water and fat content of a material with known curd content such as butter as it emerges from the manufacturing process comprising:
   continuously measuring the dielectric constant of the material after it emerges from the manufacturing process,
   continuously measuring the density of the material after it emerges from the manufacturing process,
   continuously calculating the water and fat content of the material by comparing the measured dielectric constant, the measured density and the known curd content to calibration values determined from prior laboratory tests.

2. A non-destructive method for continuously determining the water, fat and salt content of a material with known curd content such as salted butter as it emerges from a manufacturing process using brine as a source of salt comprising:
   continuously measuring the dielectric constant of the material after it emerges from the manufacturing process,
   continuously measuring the density of the material after it emerges from the manufacturing process,
   continuously measuring the brine flow into the manufacturing process,
   continuously measuring the velocity of the material outflow from the manufacturing process,
   using the measured density and the measured velocity to determine the mass flow of the material,
   comparing the brine flow to the mass flow to determine the salt content of the material,
   calculating the water, fat and salt content of the material by comparing the measured dielectric constant, the measured density, the measured velocity, the measured brine flow, and the known curd content to calibration values determined from prior laboratory tests.

3. A non-destructive method for continuously determining the water and fat content of a material with known curd content such as butter as it emerges from a manufacturing process comprising:
   continuously measuring the density of the material after it emerges from the manufacturing process,
   irradiating the material as it emerges from the manufacturing process with low energy X or gamma ray radiation,
   continuously measuring the intensity of low energy X or gamma ray radiation backscattered from the material as it is irradiated,
   continuously calculating the water and fat content by comparing measured density, the measured backscattered intensity, the known curd content to calibration values determined from prior laboratory tests.

4. A non-destructive method for continuously determining the water, fat, and salt content of a material with known curd content such as salted butter as it emerges from the manufacturing process using brine as a source of salt comprising:
  continuously measuring the density of the material after it emerges from the manufacturing process,
  irradiating the material as it emerges from the manufacturing process with low energy X or gamma ray radiation,
  continuously measuring the intensity of backscattered soft X-ray or gamma radiation from the material as it is irradiated,
  continuously measuring the velocity of the material as it emerges from the manufacturing process;
  calculating the mass flow of the material as it emerges from the manufacturing process;
  continuously measuring the brine flow into the manufacturing process;
  calculating the water, fat, and salt content by comparing the measured density, the measured velocity, the measured backscattered X-ray intensity, the known curd content, and the measured brine flow to calibration values determined from prior laboratory tests.

5. A non-destructive method for continuously determining the water, fat and salt content of a material with a known curd content, such as salted butter, as it emerges from a manufacturing process using brine as a source of salt comprising;
  continuously measuring the density of the material after it emerges from a manufacturing process;
  continuously measuring the velocity of the material outlflow from the manufacturing process,
  calculating the instantaneous mass flow of the material as it emerges from the manufacturing process,
  continuously measuring the brine flow into the manufacturing process,
  continuously measuring the dielectric constant of the material after it emerges from the manufacturing process,
  irradiating the material as it emerges from the manufacturing process with low energy X or gamma ray radiation,
  continuously measuring the intensity of low energy X or gamma ray radiation backscattered from the material as it is irradiated,
  continuously calculating the water, fat and salt content by comparing calculated mass flow, the measured brine flow and dielectric constant, the measured backscattered intensity, the known curd content to calibration values determined from prior laboratory tests.

6. A non-destructive method for determining the water, salt and fat content of a material with known curd content, such as butter, as it emerges from a manufacturing process comprising:
  measuring the instantaneous dielectric constant of the material after it emerges from a manufacturing process,
  measuring the instantaneous density of the material after it emerges from the manufacturing process,
  irradiating the material as it emerges from the manufacturing process with low energy X or gamma ray radiation,
  measuring the intensity of low energy X or gamma ray radiation backscattered from the material as it is irradiated,
  calculating the water, salt and fat content by comparing the measured instantaneous dielectric constant, the measured instantaneous density, the measured backscattered intensity, the known curd content to calibration values determined from prior laboratory tests.

7. A non-destructive method for continuously determining the water, salt and fat content of a material with known curd content, such as butter, as it emerges from a manufacturing process comprising:
  continuously measuring the dielectric constant of the material after it emerges from a manufacturing process,
  continuously measuring the density of the material after it emerges from the manufacturing process,
  irradiating the material as it emerges from the manufacturing process with low energy X or gamma ray radation,
  continuously measuring the intensity of low energy X or gamma ray radiation backscattered from the material as it is irradiated,
  continuously calculating the water, salt and fat content by comparing the measured dielectric constant, the measured density, the measured backscattered intensity, the known curd content to calibration values determined from prior laboratory tests.

8. A non-destructive method for determining the water and fat content of a material with known curd content, such as butter, as it emerges from a manufacturing process comprising:
  measuring the instantaneous dielectric constant of the material after it emerges from a manufacturing process,
  measuring the instantaneous density of the material after it emerges from the manufacturing process,
  calculating the water and fat content of the material by comparing the measured instantaneous dielectric constant, the measured instantaneous density and the known curd content to calibration values determined from prior laboratory tests.

9. A non-destructive method for determining the water, fat and salt content of a material with known curd content, such as salted butter, as it emerges from a manufacturing process using brine as a source of salt comprising:
  continuously measuring the dielectric constant of the material after it emerges from a manufacturing process,
  measuring the instantaneous density of the material after it emerges from the manufacturing process,
  measuring the instantaneous brine flow into the manufacturing process,
  measuring the instantaneous velocity of the material outflow from the manufacturing process,
  using the measured density and the measured velocity to determine the mass flow of the material,
  comparing the brine flow to the mass flow to determine the salt content of the material,
  calculating the water, fat and salt content of the material by comparing the measured dielectric constant, the measured density, the measured velocity, the measured brine flow, and the known curd content to calibration values determined from prior laboratory tests.

10. A non-destructive method for determining the water and fat content of a material with known curd content such as butter as it emerges from a manufacturing process comprising:

measuring the instantaneous density of the material after it emerges from a manufacturing process, irradiating the material as it emerges from the manufacturing process with low energy X or gamma ray radiation, measuring the instantaneous intensity of low energy X or gamma ray radiation backscattered from the material as it is irradiated, calculating the water and fat content by comparing the measured instantaneous density, the measured backscattered intensity, the known curd content to calibration values determined from prior laboratory tests.

11. A non-destructive method for determining the water, fat and salt content of a material with a known curd content, such as salted butter, as it emerges from a manufacturing process using brine as a source of salt comprising:

measuring the instantaneous density of the material after it emerges from a manufacturing process, measuring the instantaneous velocity of the material outflow from the manufacturing process, measuring the instantaneous brine flow into the manufacturing process, measuring the instantaneous dielectric constant of the material after it emerges from the manufacturing process, irradating the material as it emerges from the manufacturing process with low energy X or gamma ray radiation, measuring the instantaneous intensity of low energy X or gamma ray radiation backscattered from the material as it is irradiated, calculating the water and fat content by comparing measured density, the measured brine flow and backscattered intensity, the known curd content to calibration values determined from prior laboratory tests.

12. A non-destructive method for determining the water, fat and salt content of a material with known curd content such as salted butter as it emerges from a manufacturing process using brine as a source of salt comprising:

measuring the instantaneous density of the material after it emerges from the manufacturing process, irradiating the material as it emerges from the manufacturing process with low energy X or gamma ray radiation, measuring the intensity of backscattered X-ray or gamma ray radiation from the material as it is irradiated, measuring the instantaneous velocity of the material as it emerges from the manufacturing process, calculating the instantaneous mass flow of the material as it emerges from the manufacturing process, measuring the instantaneous brine flow into the manufacturing process, calculating the water, fat and salt content by comparing the measured instantaneous density, the measured instantaneous velocity, the measured backscattered X-ray intensity, the known curd content and the measured instantaneous brine flow to calibration values determined from prior laboratory tests.

* * * * *